United States Patent [19]

Yasuda et al.

[11] Patent Number: 4,983,723
[45] Date of Patent: Jan. 8, 1991

[54] CYCLOALKANE DERIVATIVES

[75] Inventors: Hitoshi Yasuda; Chikara Fukaya; Kanemichi Okano; Kazumasa Yokoyama, all of Osaka, Japan

[73] Assignee: Green Cross Corporation, Osaka, Japan

[21] Appl. No.: 129,217

[22] Filed: Dec. 7, 1987

[30] Foreign Application Priority Data

Dec. 5, 1986 [JP] Japan .................. 61-290785
Dec. 5, 1986 [JP] Japan .................. 61-290786

[51] Int. Cl.$^5$ .................. A61K 31/00; C07C 13/00
[52] U.S. Cl. .................. 536/4.100; 514/927; 568/376; 585/20
[58] Field of Search .................. 536/4.1; 514/54, 927, 514/53; 568/376; 585/20

[56] References Cited

U.S. PATENT DOCUMENTS 4,888,417 12/1989 Shiraga et al. .................. 514/927

FOREIGN PATENT DOCUMENTS 0203541 12/1986 European Pat. Off. .
0282643 9/1988 European Pat. Off. .
51-48633 4/1976 Japan .

OTHER PUBLICATIONS

Chemical Abstracts, vol. 85, 1976, p. 480, Abstract No. 176948j.
J. Meinwald et al,. "Defense Mechanism of Arthropods: XXV. Stereospecific Synthesis of an Allenic Sesguiterpenoid from the Grasshopper Romalea microptera," Tetrahedron Letters, No. 21, Pergamon Press, 1969, pp. 1657–1660.
A. Haag et al,. "2. Synthese von (-)-(R)-4-Hydroxy-Beta-Ionon und (-)-(5R,6S)-5-Hydroxy-4,5-Dihydro-Alpha-Ionen Aus (-)-(S)-Alpha-Ionon", Helvetica Chimica Acta, vol. 63, No. 2.

Primary Examiner—Ronald W. Griffin
Assistant Examiner—Everett White
Attorney, Agent, or Firm—Sughrue, Mion, Zinn, Macpeak & Seas

[57] ABSTRACT

A cycloalkane derivative represented by the formula (I):

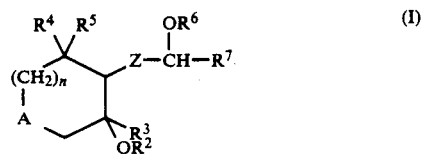

wherein A, $R^2$, $R^3$, $R^4$, $R^5$, $R^6$, $R^7$, Z, and n are as defined in the specification. The compounds of formula (I) exhibit activities against peptic ulcers and are useful as therapeutic and prophylactic agents for peptic ulcers.

6 Claims, No Drawings

CYCLOALKANE DERIVATIVES

FIELD OF THE INVENTION

This invention relates to a novel cycloalkane derivative useful as, for example, a pharmaceutical for peptic ulcers.

BACKGROUND OF THE INVENTION

Various types of therapeutic and prophylactic agents for peptic ulcers have been proposed, as described in EP No. 203541A. In order to cope with the recent tendency toward increase of ulcerations, it has been desired to develop more effective therapeutic and prophylactic agents for peptic ulcers.

SUMMARY OF THE INVENTION

As a result of extensive investigations on effective therapeutic and prophylactic agents for peptic ulcers, it has been found in the present invention that a series of compounds represented by formula (I) shown below exhibit superior activities against peptic ulcers.

More specifically, the present invention provides a cycloalkane derivative represented by formula (I):

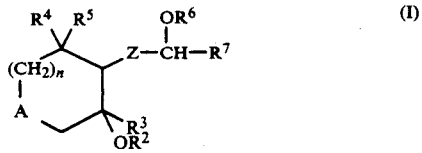

wherein A represents a methylene group, >CH—O—$R^8$, or a carbonyl group; $R^2$, $R^6$, and $R^8$ each represents a hydrogen atom or an organic residual group; $R^3$, $R^4$, and $R^5$ each represents a hydrogen atom or a substituted or unsubstituted alkyl group; $R^7$ represents a substituted or unsubstituted alkyl group; Z represents an ethylene group (—C≡C—), a vinylene group, an ethylene group, or =C=CH—; and n represents 0 or 1 and an anti-peptic ulcer composition containing the same.

DETAILED DESCRIPTION OF THE INVENTION

In formula (I), the alkyl group represented by $R^3$, $R^4$, $R^5$, and $R^7$ may be either straight or branched, and preferably contains from 1 to 7, and more preferably from 1 to 4, carbon atoms. Specific examples of the alkyl group are a methyl group, an ethyl group, an n-propyl group, an iso-propyl group, an n-butyl group, a t-butyl group, an n-pentyl group, an n-hexyl group, a heptyl group, etc. These alkyl groups may be substituted with a hydroxyl group, a carboxyl group, an amino group or a carbonyl group.

The organic residual group represented by $R^2$, $R^6$ and $R^8$ is not particularly limited as long as it is pharmacologically acceptable. Illustrative examples of such an organic residual group include an alkyl group, an acyl group, an alkoxycarbonyl group, an alkoxycarbonylalkyl group, a carboxyalkyl group, a carboxyalkylcarbonyl group, a cyclic acetal group, an oligosaccharide residue having from 1 to 3 sugar units.

The alkyl group as an organic residual group may be either straight or branched, and preferably contains from 1 to 7, and more preferably from 1 to 4, carbon atoms. Specific examples of the alkyl group include a methyl group, an ethyl group, an n-propyl group, an iso-propyl group, an n-butyl group, a t-butyl group, an n-pentyl group, an n-hexyl group, an n-heptyl group, etc.

The acyl group as an organic residual group includes aliphatic groups having from 1 to 6, and particularly from 2 to 5, carbon atoms, e.g., an acetyl group, a propionyl group, a butyryl group, a valeryl group, etc.; and aromatic groups, e.g., a benzoyl group.

The alkoxy moiety of the alkoxycarbonyl group as an organic residual group may be either straight or branched, and preferably contains from 1 to 7, and more preferably from 1 to 4, carbon atoms. Specific examples of the alkoxy group include a methoxy group, an ethoxy group, an n-propoxy group, an iso-propoxy group, an n-butoxy group, a t-butoxy group, an n-hexyloxy group, an n-heptyloxy group, etc.

The alkoxycarbonyl group as an organic residual group contains the above-enumerated alkoxy group and includes, for example, a methoxycarbonyl group, an ethoxycarbonyl group, etc.

The alkoxycarbonylalkyl group as an organic residual group contains the above-enumerated alkoxy and alkyl groups and includes, for example, a methoxycarbonylmethyl group.

The carboxyalkyl group as an organic residual group contains the above-enumerated alkyl group and includes for example, a carboxymethyl group.

The carboxyalkylcarbonyl group as an organic residual group contains the above-enumerated alkyl group and includes, for example, a carboxyethylcarbonyl group.

The cyclic acetal group as an organic residual group includes a tetrahydropyranyl group.

The oligosaccharide residue having from 1 to 3 sugar units as an organic residual group includes mono-, di-, or triglycosido residues, in which the constituting sugar units are not particularly restricted. Specific examples of the monoglycosido residue are a glucosyl group, an arabinosyl group, a galactosyl group, a mannosyl group, a fructosyl group, a xylosyl group, a ribosyl group, an apiosyl group, a glucosamine residual group, etc. Specific examples of the diglycosido residue are an apiosylglucosyl group, a sucrosyl group, a maltosyl group, a lactosyl group, a gentiobiosyl group, etc. Specific examples of the triglycosido residue include an apiosylgentiobiosyl group, a gentianosyl group, a raffinosyl group, etc. A part or all of the hydroxyl groups in these sugar moieties may be substituted with the above-recited lower alkyl, acyl, alkoxycarbonyl, alkoxycarbonylalkyl, carbonylalkyl, carboxyalkylcarbonyl or cyclic acetal groups.

The compounds of formula (I) according to the present invention can be prepared, for example, as follows.

(1) Preparation of Compounds (I-1) [(I) wherein $R^2$ and $R^6$=H; Z=vinylene group]

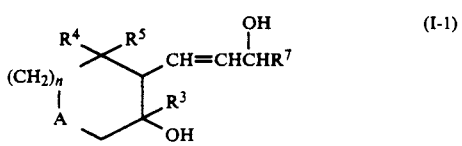

(a) Compounds (I-1) wherein A is >CHOH, and $R^7$ is an alkyl group having 2 or more carbon atoms [hereinafter referred to as Compound (I-a)] can be prepared through the following 7 steps:

Step 1:

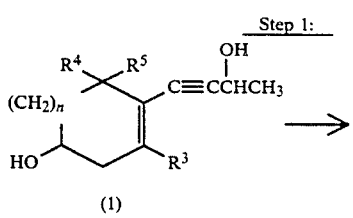

(1)

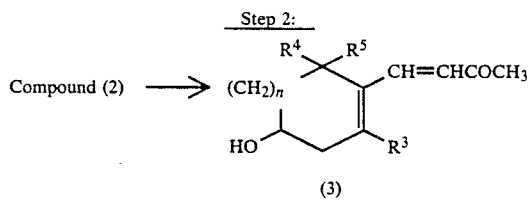

(2)

wherein $R^3$, $R^4$, $R^5$, and n are as defined above.

Step 1 is a reduction reaction. This reaction can be carried out by, for example, using a reducing agent.

For example, the reduction can preferably be effected in an inert solvent, such as an organic solvent (e.g., tetrahydrofuran, diglyme, etc.) in the presence of a reducing agent (e.g., lithium aluminum hydride) usually at a temperature ranging from about 60° to 150° C., and preferably around 120° C., for a period of from about 10 to 20 hours, and preferably about 15 hours. It is preferable to conduct the reaction under a refluxing condition and/or in an inert gas atmosphere (e.g., nitrogen, argon, etc.).

Step 2:

Compound (2) ⟶ 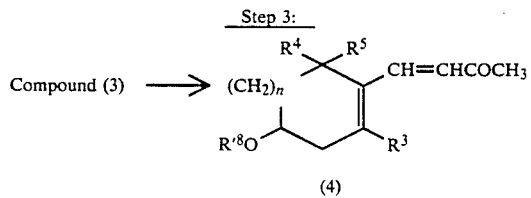

(3)

wherein $R^3$, $R^4$, $R^5$, and n are as defined above.

Step 2 is an oxidation reaction. Suitable oxidizing agents to be used include manganese dioxide. This reaction is preferably carried out in an inert solvent, such as an organic solvent (e.g., acetone) usually at a temperature of from room temperature to about 60° C., and preferably from about 40° to 50° C., for a period of from about 12 to 36 hours, and preferably about 24 hours.

Step 3:

Compound (3) ⟶

CH=CHCOCH₃ structure (4)

wherein $R^3$, $R^4$, $R^5$, and n are as defined above; and $R'^8$ represents a protective group.

In Step 3, the hydroxyl group of Compound (3) is protected with a protective group preferably including a silyl group (e.g., a trialkylsilyl group).

In the case of using a silyl protective group, a silylating agent to be used preferably includes a trialkylhalosilane, e.g., trimethylchlorosilane, t-butyldimethylchlorosilane, etc.

The silylation reaction is preferably performed in the presence of a base, such as imidazole. The silylation is preferably carried out in an inert solvent, such as an organic solvent (e.g., dimethylformaldehyde, etc.) usually at a temperature ranging from about 15° to 25° C., and preferably around room temperature, for a period of from about 10 to 20 hours, and preferably about 15 hours. This reaction is preferably conducted in an inert gas atmosphere, e.g., nitrogen, argon, etc.

Step 4:

Compound (4) ⟶ 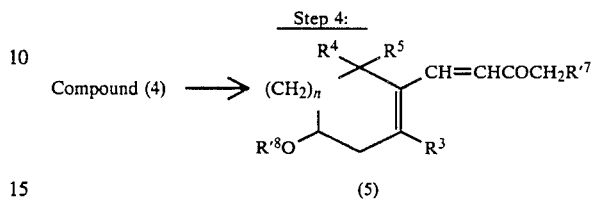

(5)

wherein $R^3$, $R^4$, $R^5$, $R'^8$, and n are as defined above; and $R'^7$ represents an alkyl group having carbon atoms less by one than that of the alkyl group represented by $R^7$.

Step 4 is an alkylation reaction. The alkylating agent to be used includes alkyl halides comprising a halogen atom (e.g., an iodine atom) and an alkyl group having, e.g., from 1 to 6 carbon atoms.

This reaction is preferably carried out in an inert solvent, such as an organic solvent (e.g., tetrahydrofuran) in the presence of hexamethylphosphoric triamide (hereinafter "HMPA") and/or a base, e.g., lithium diisopropylamide (hereinafter "LDA"). The reaction time usually ranges from about 6 to 20 hours, and preferably about 15 hours. The reaction temperature usually ranges from about −80° to 0° C., and preferably about −78° C. Further, the reaction is preferably conducted in an inert gas atmosphere.

Step 5:

Compound (5) ⟶ 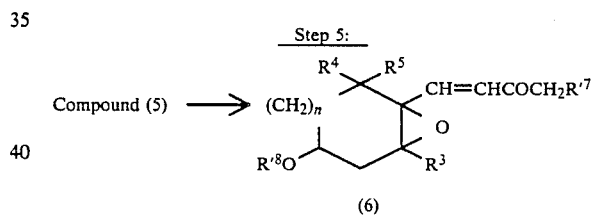

(6)

wherein $R^3$, $R^4$, $R^5$, $R'^7$, $R'^8$, and n are as defined above.

Step 5 is an epoxidation reaction of the carbon double bond of Compound (5). The epoxidizing agent to be used includes m-chloroperbenzoic acid.

This reaction is preferably carried out in an inert solvent, such as an organic solvent (e.g., chloroform) usually at a temperature of from about −20° to 0° C., and preferably under ice-cooling, for a period of from about 1 to 10 hours, and preferably from about 5 to 8 hours.

Step 6:

Compound (6) ⟶ 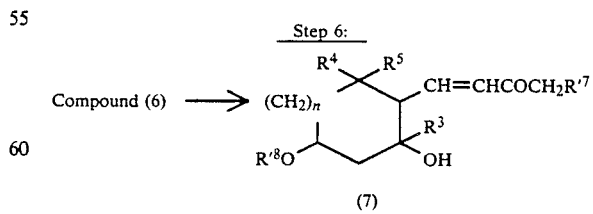

(7)

wherein $R^3$, $R^4$, $R^5$, $R'^7$, $R'^8$, and n are as defined above.

Step 6 is a reduction reaction for cleaving the epoxy ring of Compound (6).

This reaction is carried out in the presence of a reducing agent, e.g., a zinc-acetic acid system, at a temperature of from about 10° to 50° C., and preferably at about 40° C., for a period of from about 1 to 10 hours, and preferably about 5 hours.

Step 7:

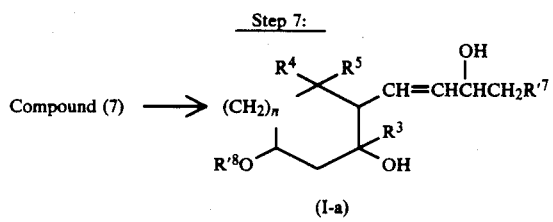

wherein $R^3$, $R^4$, $R^5$, $R'^7$, and n are as defined above.

Step 7 is a reduction reaction of the keto group of Compound (7). The reaction can be carried out in a known manner generally using a reducing agent for enones, including sodium borohydride, etc. This reaction is preferably effected in an inert solvent, such as an organic solvent (e.g., methanol) usually at a temperature of from about $-20°$ to $25°$ C., and preferably about $0°$ C., for a period of from about 1 to 10 hours, and preferably from about 5 to 8 hours. (b) Compounds of formula (I-1) wherein A is $>$CHOH and $R^7$ is a methyl group, i.e., compounds of formula (I-b):

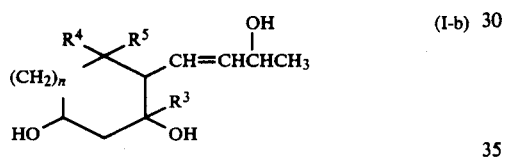

wherein $R^3$, $R^4$, $R^5$, and n are as defined above, can be prepared in the same manner as for Compounds (I-a), except for excluding Step 4.

(c) Compounds of formula (I-1) wherein A is a methylene group and $R^7$ is an alkyl group having 2 or more carbon atoms, i.e., compounds of formula (I-c):

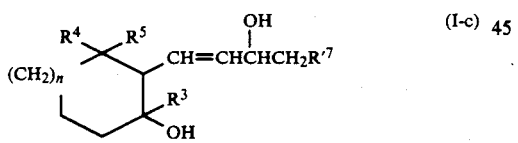

wherein $R^3$, $R^4$, $R^5$, $R'^7$, and n are as defined above, can be prepared in the same manner as for Compounds (I-a), except for excluding Step 3.

(d) Compounds of formula (I-1) wherein A is a methylene group and $R^7$ is a methyl group, i.e., compounds of formula (I-d):

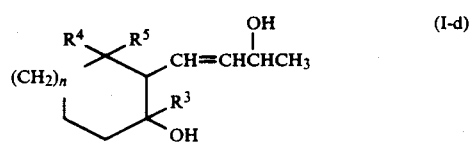

wherein $R^3$, $R^4$, $R^5$, and n are as defined above, can be prepared in the same manner as for Compounds (I-a), except for excluding Steps 3 and 4.

Preparation of Compounds (I-2) [(I) wherein $R^2$ and $R^4$=H; Z=ethynylene]

Compounds (I-2) can be prepared through the following reaction scheme starting with Compounds (I-1):

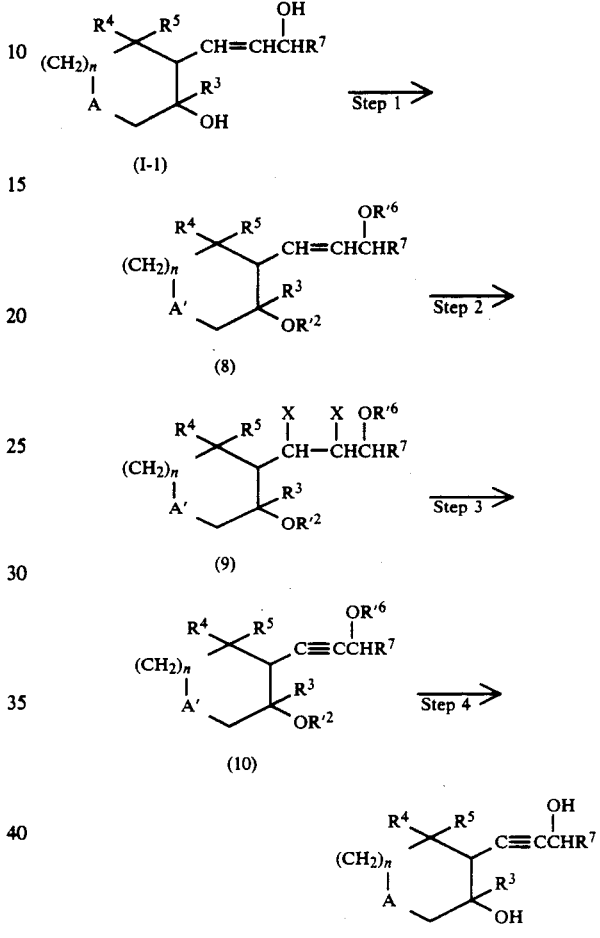

wherein A, $R^3$, $R^4$, $R^5$, $R^7$, and n are as defined above; A' represents a methylene group, a carbonyl group, or $>$CH—O—$R'^8$; $R'^2$, $R'^6$, and $R'^8$ each represents a protective group; and X represents a halogen atom (e.g., a chlorine atom, a bromine atom, etc.)

In Step 1, each of the hydroxyl groups of Compound (I-1) is protected with a protective group, such as an acyl group having, e.g., from 2 to 4 carbon atoms (e.g., an acetyl group, a propionyl group, etc.), a benzoyl group, a tetrahydropyranyl group, etc.

For protection with an acyl group for example, the acylating agent to be used includes a corresponding carboxylic acid or a known reactive derivative thereof. Preferred reactive derivatives of carboxylic acids includes acid halides (particularly acid chlorides and acid bromides). The acylation is preferably effected in the presence of a base, such as a trialkylamine (e.g., triethylamine), a pyridine (e.g., p-dimethylaminopyridine), etc., as an acid scavenger.

The acylation is preferably carried out in an inert solvent, such as an organic solvent (e.g., triethylamine), generally at a temperature of from about $-20°$ to $25°$ C., and preferably from about 0° to 25° C., for a period of from about 6 to 18 hours, and preferably about 15 hours.

Step 2 is a halogen-addition reaction to the carbon double bond of Compound (8). The halogenating agent to be used preferably includes halogen molecules (e.g., bromine molecules). This reaction is preferably carried out in an inert solvent, such as an organic solvent (e.g., carbon tetrachloride), usually at a temperature of from about −20° to 0° C., and preferably from about −5° to 0° C., for a period of from about 0.5 to 5 hours, and preferably from about 0.5 to 2 hours.

In Step 3, Compound (9) is dehydrohalogenated by an alkoxide (e.g., potassium t-butoxide).

This reaction can be carried out preferably in an inert solvent, such as an organic solvent (e.g., dimethyl sulfoxide), usually at a temperature of from about 40° to 60° C., and preferably about 50° C., for a period of from about 0.5 to 3 hours, and preferably from about 0.5 to 2 hours.

Step 4 is a reaction in which the protective groups are eliminated by a method appropriately selected depending on the kind of the respective protective group to be released. For example, the acyl group can generally be released through reaction with an alkali salt (e.g., potassium carbonate).

The elimination reaction is preferably carried out in an inert solvent, such as an organic solvent (e.g., methanol), usually at a temperature of from about −20° to 0° C., and preferably about 0° C., for a period of from about 1 to 7 hours, and preferably about 5 hours.

(3) Preparation of Compounds (I-3) [(I) wherein $R^2$, $R^6$, and/or $R^8$ each represents an organic residual group; and Z represents a vinylene group or an ethylene group]

Compounds (I-3) can be derived from the compounds (I-1) and (I-2) in a known manner selected depending on the organic residual group to be introduced.

For example, compounds (I-3) wherein $R^2$, $R^6$, and $R^8$ each represents an alkyl group can be obtained by alkylating the compounds (I-1) or (I-2). The alkylating agent to be used preferably includes alkyl halides (e.g., methyl iodide), alkyl sulfates (e.g., dimethyl sulfate), and the like. The alkylation is preferably carried out in an inert solvent (e.g., tetrahydrofuran, dimethyl sulfoxide, N,N-dimethyl formamide, etc.) in the presence of a base (e.g., sodium hydride, silver oxide, potassium carbonate, sodium carbonate, etc.). The reaction temperature usually ranges from about 0° to 80° C., and the reaction time usually ranges from about 0.5 to 5 hours.

Compounds (I-3) wherein $R^2$, $R^6$, and $R^8$ each represents an acyl group can be prepared by acylating the compounds (I-1) or (I-2). The acylating agent to be used preferably includes a carboxylic acid and a known reactive derivative thereof, such as an acid halide (e.g., an acid chloride, and acid bromide), an acid anhydride, an active ester, and the like. In the case of using a carboxylic acid as an acylating agent, the acylation is preferably effected in the presence of a condensing agent, such as dicyclohexylcarbodiimide. In the case of using other acylating agents, the reaction is preferably effected in the presence of a tertiary amine, such as pyridine, triethylamine, etc. In either case, the reaction may be conducted in the presence of an inert solvent, e.g., chloroform, dichloromethane, tetrahydrofuran, etc. The reaction temperature usually ranges from about 0° to 25° C., and the reaction time usually ranges from about 0.5 to 5 hours.

4) Preparation of Compounds (I-4) [(I) wherein $R^2$, $R^6$, and $R^8$ each represents a hydrogen atom; and Z represents =C=CH—]

Compounds (I-4) can be prepared through Reaction Scheme A or B. shown below:

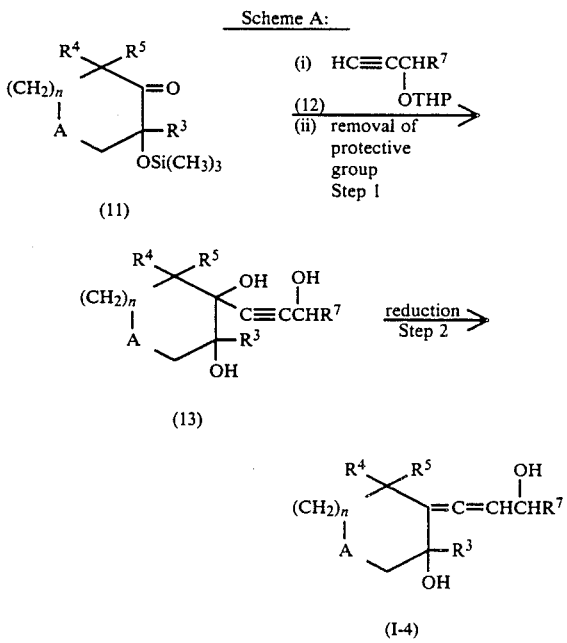

wherein A, $R^3$, $R^4$, $R^5$, $R^7$, and n are as defined above.

In Step 1, the reaction is preferably carried out in the presence of a base, such as n-butyl lithium, lithium diisopropylamide, etc.

This reaction is preferably effected in an inert gas atmosphere (e.g., nitrogen, argon, etc.) and/or in the presence of an inert solvent, such as an organic solvent (e.g., tetrahydrofuran). The reaction temperature usually ranges from about −80° to 0° C., and preferably from about −78° to 0° C., and the reaction time usually ranges from about 3 to 7 hours, and preferably about 5 hours.

The hydroxyl groups in Compounds (11) and (12) are preferably protected in advance with, for example, a trialkylsilyl group (e.g., a trimethylsilyl group), a cyclic ether group (e.g., tetrahydropyranyl group), etc. in accordance with a known method.

After completion of the reaction of Step 1, the protective groups are removed by a known means. For example, the trialkylsilyl group can easily be removed by reacting with water, preferably methanolic hydrochloric acid, and more preferably 1N hydrochloric acid. The cyclic ether group can also be removed similarly.

Step 2 is a reduction reaction. The reduction may be effected by using a reducing agent, such as lithium aluminum hydride.

This reaction can preferably be carried out in an inert solvent, such as an organic solvent (e.g., tetrahydrofuran, diethyl ether, etc.) in an inert gas atmosphere. The reaction temperature usually ranges from about 35° to 70° C., and preferably at reflux, and the reaction time usually ranges from about 5 to 20 hours, and preferably from 10 to 15 hours.

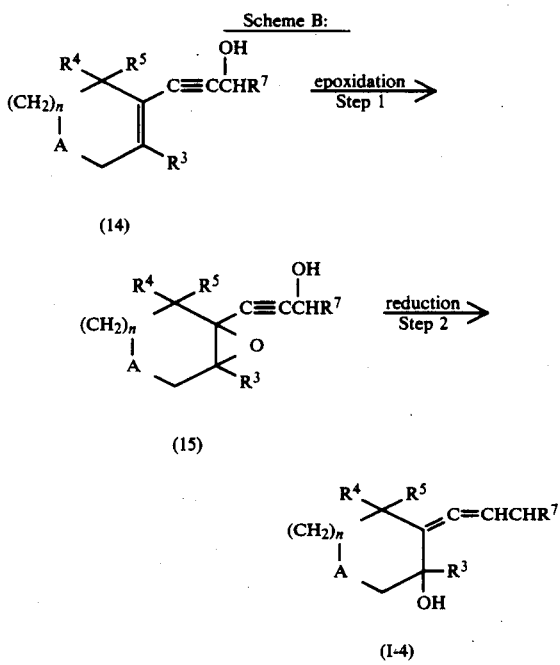

wherein A, $R^3$, $R^4$, $R^5$, $R^7$, and n are as defined above.

Step 1 is an epoxidation of the carbon double bond. The epoxidizing agent to be used preferably includes m-chloroperbenzoic acid.

This reaction is preferably carried out in an inert solvent, such as an organic solvent (e.g., chloroform) usually at a temperature of from about $-20°$ to $10°$ C., and preferably about $0°$ C., for a period of from about 1 to 10 hours, and preferably from about 5 to 8 hours.

It is preferably that the hydroxyl group of Compound (14) be previously protected with, for example, an acyl group (e.g., an acetyl group).

Step 2 is a general reduction reaction. The reduction is preferably effected by using a reducing agent, such as lithium aluminum hydride.

This reaction is preferably carried out in an inert solvent, such as an organic solvent (e.g., tetrahydrofuran) in an inert gas atmosphere (e.g., nitrogen, argon, etc.). The reaction time usually ranges from about 5 to 15 hours, and preferably from about 8 to 10 hours, and the reaction temperature usually ranges from about $35°$ to $70°$ C., and preferably at reflux.

(5) Preparation of Compounds (I-5) [(I) wherein $R^2$, $R^6$ and/or $R^8$ each represents an organic residual group]

Compounds (I-5) can be derived from the comounds (I-4) in a known manner selected depending on the organic residual group to be introduced.

For example, compounds wherein $R^2$, $R^6$, and $R^8$ each represents an alkyl group can be obtained by alkylating the compounds (I-4). The alkylating agent to be used preferably includes alkyl halides (e.g., methyl iodide), alkyl sulfates (e.g., dimethyl sulfate), and the like. The alkylation is preferably carried out in an inert solvent (e.g., acetone, chloroform, dichloromethane, tetrahydrofuran, dimethyl sulfoxide, N,N-dimethyformamide, etc.) in the presence of a base (e.g., sodium hydride, silver oxide, potassium carbonate, sodium carbonate, etc.). The reaction temperature usually ranges from about $0°$ to $100°$ C., and preferably from about $0°$ to $80°$ C., and the reaction time usually ranges from about 0.5 to 10 hours, and preferably from 0.5 to 5 hours.

Compounds wherein $R^2$, $R^6$, and $R^8$ each represents an acyl group can be prepared by acylating the compunds (I-4). The acylating agent to be used preferably includes a corresponding carboxylic acid and a known reactive derivative thereof, such as an acid halide (e.g., an acid chloride, and acid bromide), an acid anhydride, an active ester, and the like. In the case of using a carboxylic acid as an acylating agent, the acylation is preferably effected in the presence of a condensing agent, such as dicyclohexylcarbodiimide. In the case of using other acylating agents, the reaction is preferably effected in the presence of a tertiary amine, such as pyridine, and triethylamine. In either case, the reaction may be conducted in the presence of an inert solvent, e.g., chloroform, dichloromethane, tetrahydrofuran, etc. The reaction temperature usually ranges from about $0°$ to $70°$ C., and preferably from about $0°$ to $25°$ C., and the reaction time usually ranges from about 0.5 to 15 hours, and preferably from about 0.5 to 5 hours.

The thus prepared compounds of formula (I) can be isolated and purified to have an arbitrary purity by known techniques, such as solvent transfer, recrystallization, chromatography, and the like.

The compounds according to the present invention exhibit activities against peptic ulcers in mammals, e.g., humans, horses, dogs, mice, rats, etc., and are, therefore, useful as therapeutic and prophylactic agents for peptic ulcers.

The compounds of the present invention can be administered through oral or non-oral route. In the case of oral administration, they are appropriately mixed with pharmaceutically acceptable additives, such as carriers, vehicles, diluents, and the like, and formulated into powders, tablets, capsules, troches, liquors, syrups, granules, and the like. In the case of non-oral administration, they are formulated into aqueous solutions or non-aqueous suspensions suitable as injections for intravenous injection, intramuscular injection, subcutaneous injection, etc. or suppositories, etc.

The dose level of the compound of the invention varies depending on the symptoms, body weight, and age of patients, and the like. For the treatment of ulcers, the compound is suitably administered at a dose ranging from 0.001 to 0.1 mg/Kg of body weight per day for adults in a single dose or several divided doses.

The present invention will now be illustrated in greater detail with reference to the following examples, but it should be understood that the present invention is not deemed to be limited thereto. In these examples, all percents are by weight unless otherwise idicated.

EXAMPLE 1

(1) Synthesis of 4-(4-Hydroxy-2,6,6-Trimethylcyclohex-1-enyl)But-3-en-2-ol

To a suspension of 1.1 g of lithium aluminum hydride in 30 ml of anhydrous diglyme and 10 ml of anhydrous tetrahydrofuran (hereinafter "THF") was added dropwise 10 ml of an anhydrous THF solution containing 5 g of 4-(4-hydroxy-2,6,6-trimethylcyclohex-1-enyl)but-3-yn-2-ol in a nitrogen atmosphere, and the mixture was stirred at reflux for 15 hours. After completion of the reaction, the reaction mixture was cooled and carefully hydrolyzed with water under ice-cooling. The aqueous phase was neutralized with diluted hydrochloric acid and extracted with diethyl ether. The organic layers were combined, washed with water, and dried over anhydrous magnesium sulfate. The solvent, etc. were removed by distillation under reduced pressure, and the residue was purified by silica gel column chromatography to obtain 2.8 g (yield: 55%) of 4-(4-hydroxy-2,6,6-trimethylcyclohex-1-enyl)but-3-en- 2-ol.

IR $\nu_{max}^{CHCl_3}$ cm$^{-1}$: 3600, 3330

(2) Synthesis of 4-(4-Hydroxy-2,6,6-Trimethylcyclohex-1-enyl)But-3-en-2-one

In 50 ml of anhydrous acetone was dissolved 2.5 g of 4-(4-hydroxy-2,6,6-trimethylcyclohex-1-enyl)but-3-en-2-ol, and 10.4 g of activated manganese dioxide was added to the solution, followed by heating at 40° to 50° C. for 24 hours while vigorous stirring. After completion of the reaction, the reaction mixture was allowed to cool to room temperature, and any insoluble matter was removed by filtration. The filtrate was concentrated under reduced pressure, and the residue was purified by silica gel column chromatography to obtain 1.5 g (yield: 60%) of 4-(4-hydroxy-2,6,6-trimethylcyclohex-1-enyl)-but-3-en-2-one.

IR $\nu_{max}^{CHCl_3}$ cm$^{-1}$: 3300, 1680

(3) Synthesis of 4-[4-(t-Butyldimethylsilyl)oxy-2,6,6-Trimethylcyclohex-1-enyl]But-3-en-2-ol To 30 ml of an anhydrous dimethylformamide (hereinafter "DMF") solution containing 588 mg of imidazole and 1.2 g of 4-(4-hydroxy-2,6,6-trimethylcyclohex-1-enyl)but-3-en-2-one was added dropwise 15 ml of an anhydrous DMF solution containing 1.3 g of t-butyldimethylchlorosilane at room temperature in a nitrogen atmosphere. After the dropwise addition, the mixture was stirred under the same conditions for 15 hours. Diethyl ether was added to the reaction mixture, and the mixture was washed several times with water cooled with ice. The organic layer was dried over anhydrous magnesium sulfate, and the solvent, etc. were removed by distillation under reduced pressure. The residue was purified by silica gel column chromatography to obtain 1.5 g (yield: 78%) of 4-[4-(t-butyldimethylsilyl)oxy-2,6,6-trimethylcyclohex-1-enyl]-but-3-en-2-one.

IR $\nu_{max}^{CHCl_3}$ cm$^{-1}$: 1680

(4) Synthesis of 4-[4-(t-Butyldimethylsilyl)oxy-1,2-Epoxy-2,2,6-Trimethylcyclohexyl]But-3-en-2-one To 20 ml of an anhydrous chloroform solution containing 1.0 g of 4-[4-(t-butyldimethylsilyl)oxy-2,6,6-trimethylcyclohex-1-enyl]but-3-en-2-one was added 616 mg of m-chloroperbenzoic acid under ice-cooling, followed by stirring at the same temperature for 8 hours. After completion of the reaction, the reaction mixture was washed several times with a saturated aqueous solution of sodium hydrogen carbonate. The organic layer was washed with a saturated aqueous solution of sodium chloride and then, with water, and dried over anhydrous magnesium sulfate. The solvent, etc. were removed by distillation under reduced pressure, and the residue was purified by silica gel column chromatography to obtain 644 mg (yield: 70%) of 4-[4-(t-butyldimethylsilyl)oxy-1,2-epoxy-2,6,6-trimethylcyclohexyl]but-3-en-2-one.

IR $\nu_{max}^{CHCl_3}$ cm$^{-1}$: 1680

(5) Synthesis of 4-(2,4-Dihydroxy-2,6,6-Trimethylcyclohexyl)But-3-en-2-one

To 50 ml of a glacial acetic acid solution containing 600 mg of 4-[4-(t-butyldimethylsilyl)oxy-1,2-epoxy-2,6,6-trimethylcyclohexyl]but-3-en-2-one was added 8.9 g of a zinc powder at room temperature, and the mixture was vigorously stirred for 5 hours while maintaining the reaction temperature at about 40° C. To the reaction mixture was added 120 ml of chloroform, followed by stirring vigorously. Any insoluble matter was separated by filtration, and the filtrate was washed successively with water, a 5% aqueous solution of sodium hydrogen carbonate and water. The organic layer was dried over anhydrous magnesium sulfate, and the solvent, etc. were removed by distillation under reduced pressure. Purification of the resiude by silica gel chromatography gave 241 mg (yield: 55%) of 4-(2,4-dihydroxy-2,6,6-trimethylcyclohexyl)but-3-en-2-one.

IR $\nu_{max}^{CHCl_3}$ cm$^{-1}$: 3350, 1680

(6) Synthesis of 4-(2,4-Dihydroxy-2,6,6-Trimethylcyclohexyl)But-3-en-2-ol

To 20 ml of a methanol solution containing 200 mg of 4-(2,4-dihydroxy-2,6,6-trimethylcyclohexyl)but-3-en-2-one was added 40 mg of sodium borohydride under ice-cooling, and the mixture was stirred at room temperature for 5 hours. After completion of the reaction, the reaction mixture was treated with acetic acid, and the solvent, etc. were removed by distillation under reduced pressure. Ethyl acetate was added to the residue, followed by washing with a saturated sodium chloride aqueous solution and then, with water. The organic layer was dried over magnesium sulfate, and the ethyl acetate was removed by distillation. The residue was purified by silica gel column chromatography to obtain 646 mg (yield: 73%) of 4-(2,4-dihydroxy-2,6,6-trimethylcyclohexyl)but-3-en-2-ol.

IR $\nu_{max}^{CHCl_3}$ cm$^{-1}$: 3600, 3350

EXAMPLE 2

(1) Synthesis of 1-[4-(t-Butyldimethylsilyl)oxy-2,6,6-Trimethylcyclohex-1-enyl]Pent-1-en-3-one To 3 ml of an anhydrous THF solution containing 375 mg of diisopropylamine was added 2.3 ml of a 1.6M n-hexane solution of n-butyl lithium at 0° C. in a nitrogen atmosphere to prepare LDA in the usual manner. The reaction mixture was cooled to −78° C., and 111 mg of hexamethylphosphoric triamide was added thereto. To the cooled mixture was dropwise added 10 ml of an anhydrous THF solution containing 1.0 g of 4-[4-(t-butyldimethylsilyl)oxy-2,6,6-trimethylcyclohex-1-enyl]-but-3-en-2-one. After the dropwise addition, the mixture was stirred under the same condition for 30 minutes. Then, 5 ml of an anhydrous THF solution of 659 mg of methyl iodide was added dropwise thereto. The reaction mixture was warmed to 0° C., followed by stirring overnight. After completion of the reaction, the reaction mixture was poured into a saturated ammonium chloride aqueous solution and extracted with diethyl ether. The organic layer was washed successively with a saturated sodium chloride aqueous solution and water, and dried over anhydrous magnesium sulfate. The solvent, etc. were removed by distillation under reduced pressure. Purification of the residue by silica gel column chromatography yielded 657 mg (63%) of 1-[4-(t-butyldimethylsilyl)oxy-2,6,6-trimethylcyclohex-1-enyl]pent-1-en-3-one.

IR $\nu_{max}^{CHCl_3}$ cm$^{-1}$: 1680

(2) Synthesis of 1-(2,4-Dihydroxy-2,6,6-Trimethylcyclohexyl)Pent-1-en-3-ol

The entitled compound was prepared from 1-[4-(t-butyldimethylsilyl)oxy-2,6,6-trimethylcyclohex-1-enyl]pent-1-en-3-one in the same manner as described in Example 1-(4), (5), and (6).

IR $\nu_{max}^{CHCl_3}$ cm$^{-1}$: 3600, 3350

EXAMPLE 3

Synthesis of 1-[4-(t-Butyldimethylsilyl)oxy-2,6,6-Trimethylcyclohex-1-enyl]Hex-1-en-3-one The entitled compound was prepared from 4-[4-(t-butyldimethylsilyl)oxy-2,6,6-trimethylcyclohex-1-enyl]but-3-en-2-one and ethyl iodide in the same manner as described in Example 2-(1).

IR $\nu_{max}^{CHCl_3}$ cm$^{-1}$: 1680

(2) Synthesis of 1-(2,4-Dihydroxy-2,6,6-Trimethylcyclohexyl)Hex-1-en-3-ol

The entitled compound was prepared from 1-[4-(t-butyldimethylsilyl)oxy-2,6,6-trimethylcyclohex-1-enyl)]hex-1-en-3-one in the same manner as described in Example 1-(4), (5), and (6).

IR $\nu_{max}^{CHCl_3}$ cm$^{-1}$: 3600, 3350

EXAMPLE 4

(1) Synthesis of 1-[4-(t-Butyldimethylsilyl)oxy-2,6,6-Trimethylcyclohex-1-enyl]Oct-1-en-3-one The entitled compound was prepared from 4-[4-(t-butyldimethylsilyl)oxy-2,6,6-trimethylcyclohex-1enyl]-but-3-en-2-one and n-butyl iodide in the same manner as described in Example 2-(1).

IR $\nu_{max}^{CHCl_3}$ cm$^{-1}$: 1680

(2) Synthesis of 1-(2,4-Dihydroxy-2,6,6-Trimethylcyclohexyl)Oct-1-en-3-ol

The entitled compound was prepared from 1-[4-(t-butyldimethylsilyl)oxy-2,6,6-trimethylcyclohex-1enyl-]oct-1-en-3-one in the same manner as described in Example 1-(4), (5), and (6).

IR $\nu_{max}^{CHCl_3}$ cm$^{-1}$: 3600, 3350

EXAMPLE 5

(1) Synthesis of 1-(2,6,6-Trimethylcyclohex-1-enyl)Pent-1-en-3-one

The entitled compound was obtained from β-ionone and methyl iodide in the same manner as described in Example 2-(1).

IR $\nu_{max}^{CHCl_3}$ cm$^{-1}$: 1675

(2) Synthesis of 1-(2-Hydroxy-2,6,6-Trimethylcyclohexyl)Pent-1-en-3-ol

The entitled compound was obtained from 1-(2,6,6-trimethylcyclohex-1-enyl)pent-1-en-3-one in the same manner as described in Example 1-(4), (5), and (6).

IR $\nu_{max}^{CHCl_3}$ cm$^{-1}$: 3330

EXAMPLE 6

(1) Synthesis of 1-(2,6,6-Trimethylcyclohex-1-enyl)Hex-1-en-3-one

The entitled compound was obtained from β-ionone and ethyl iodide in the same manner as described in Example 2-(1).

IR $\nu_{max}^{CHCl_3}$ cm$^{-1}$: 1675

(2) Synthesis of 1-(2-Hydroxy-2,6,6-Trimethylcyclohexyl)Hex-1-en-3-ol

The entitled compound was prepared from 1-(2,6,6-trimethylcyclohex-1-enyl)hex-1-en-3-one in the same manner as in Example 1-(4), (5), and (6).

IR $\nu_{max}^{CHCl_3}$ cm$^{-1}$: 3330

EXAMPLE 7

Synthesis of 1-(2,6,6-Trimethylcyclohex-1-enyl)Oct-1-en-3-ol

The entitled compound was obtained from β-ionone and n-butyl iodide in the same manner as in Example 2-(1).

IR $\nu_{max}^{CHCl_3}$ cm$^{-1}$: 1675

(2) Synthesis of 1-(2-Hydroxy-2,6,6-Trimethylcyclohexyl)Oct-1-en-3-ol

The entitled compound was obtained from 1-(2,6,6-trimethylcyclohex-1-enyl)oct-1-en-3-one in the same manner as in Example 1-(4), (5), and (6).

IR $\nu_{max}^{CHCl_3}$ cm$^{-1}$: 3330

EXAMPLE 8

(1) Synthesis of 4-[3-(t-Butyldimethylsilyl)oxy-2,2,5-Trimethylcyclopent-1-enyl]But-3-en-2-one The entitled compound was obtained from 4-(3-hydroxy-2,2,5-trimethylcyclopent-5-enyl)but-3-yn-2-ol in the same manner as in Example 1-(1), (2), and (3).

IR $\nu_{max}^{CHCl_3}$ cm$^{-1}$: 1680

(2) Synthesis of 4-(2,4-Dihydroxy-2,5,5-Trimethylcyclopentyl)But-3-en-2-ol

The entitled compound was obtained from the product of Example 7-(1) in the same manner as in Example 1-(4), (5), and (6).

IR $\nu_{max}^{CHCl_3}$ cm$^{-1}$: 3600, 3330

EXAMPLE 9

(1) Synthesis of 5-[3-(t-Butyldimethylsilyl)oxy-2,5,5-Trimethylcyclopent-5-enyl]Pent-4-en-3-one The entitled compound was obtained from 4-[3-(t-butyldimethylsilyl)oxy-2,5,5-trimethylcyclopent-1-enyl]but-3-en-2-one [the product of Example 8-(1)] and methyl iodide in the same manner as in Example 2-(1).

IR $\nu_{max}^{CHCl_3}$ cm$^{-1}$: 1680

(2) Synthesis of 5-(2,4-Dihydroxy-2,5,5-Trimethylcyclopentyl)Pent-4-en-3-ol

The entitled compound was obtained from 5-[3-(t-butyldimethylsilyl)oxy-2,5,5-trimethylcyclopent-5-enyl]pent-4-en-3-one in the same manner as in Example 1-(4), (5), and (6).

IR $\nu_{max}^{CHCl_3}$ cm$^{-1}$: 3600, 3300

EXAMPLE 10

(1) Synthesis of 1-[3-(t-Butyldimethylsilyl)oxy-2,2,5-Trimethylcyclopent-5-enyl]Hexa-1-en-3-one The entitled compound was obtained from 4-[3-(t-butyldimethylsilyl)oxy-2,2,5-trimethylcyclopent-5-enyl]but-3-en-2-one and ethyl iodide in the same manner as in Example 2-(1).

IR $\nu_{max}^{CHCl_3}$ cm$^{-1}$: 1680

(2) Synthesis of 1-(2,4-Dihydroxy-2,5,5-Trimethylcyclopentyl)Hex-1-en-3-ol

The entitled compound was obtained from 1-[3-(t-butyldimethylsilyl)oxy-2,5,5-trimethylcyclopent-5-enyl]hex-1-en-3-one in the same manner as in Example (4), (5), and (6).

IR $\nu_{max}^{CHCl_3}$ cm$^{-1}$: 3330

EXAMPLE 11

(1) Synthesis of 1-[3-(t-Butyldimethylsilyl)oxy-Pent-5-enyl]Oct-1-en-3-one

The entitled compound was obtained from 4-[3-(t-butyldimethylsilyl)oxy-2,5,5-trimethylcyclopent-5-enyl]but-3-en-2-one and n-butyl iodide in the same manner as in Example 2-(1).

IR $\nu_{max}^{CHCl_3}$ cm$^{-1}$: 1680

(2) Synthesis of 1-(2,4-Dihydroxy-2,5,5-Trimethylcyclopentyl)Oct-1-en-3-ol

The entitled compound was prepared from 1-[3-(t-butyldimethylsilyl)oxy-2,5,5-trimethylcyclopent-5-enyl]hex-1-en-3-one in the same manner as in Example (4), (5), and (6).

IR $\nu_{max}^{CHCl_3}$ cm$^{-1}$: 3600, 3330

EXAMPLE 12

(1) Synthesis of 4-(2,2,5-Trimethylcyclopent-5-enyl)But-3-en-2-one

The entitled compound was obtained from 4-(2,5,5-trimethylcyclopent-5-enyl)but-3-yn-2-ol in the same manner as in Example 1-(1) and (2).

IR $\nu_{max}^{CHCl_3}$ cm$^{-1}$: 3330

(2) Synthesis of 4-(2-Hydroxy-2,5,5-Trimethylcyclopentyl)But-3-en-2-ol

The entitled compound was obtained from the product of Example 12-(1) in the same manner as in Example 1-(4), (5), and (6).

IR $\nu_{max}^{CHCl_3}$ cm$^{-1}$: 3330

EXAMPLE 13

(1) Synthesis of 1-(2,2,5-Trimethylcyclopent-5-enyl)Pent-1-en-3-one

The entitled compound was obtained from 4-(2,2,5-trimethylcyclopent-5-enyl)but-3-en-2-one [(the product of Example 12(1)] and methyl iodide in the same manner as in Example 2-(1).

IR $\nu_{max}^{CHCl_3}$ cm$^{-1}$: 1680

(2) Synthesis of 1-(2-Hydroxy-2,5,5-Trimethylcyclopentyl)Pent-1-en-3-ol

The entitled compound was obtained from 1-(2,2,5-trimethylcyclopent-5-enyl)pent-1-en-3-one in the same manner as in Example 1-(4), (5), and (6).

IR $\nu_{max}^{CHCl_3}$ cm$^{-1}$: 3330

EXAMPLE 14

(1) Synthesis of 1-(2 2,5-Trimethylcyclopent-5-enyl)Hex-1-en-3-ol

The entitled compound was obtained from 4-(2,2,5-trimethylcyclopent-5-enyl)but-3-en-2-one and ethyl iodide in the same manner as in Example 2-(1).

IR $\nu_{max}^{CHCl_3}$ cm$^{-1}$: 1680

(2) Synthesis of 1-(2-Hydroxy-2,5,5-Trimethylcyclopentyl)Hex-1-en-3-ol

The entitled compound was obtained from 1-(2,2,5-trimethylcyclopent-5-enyl)hex-1-en-3-one in the same manner as in Example 1-(4), (5), and (6).

IR $\nu_{max}^{CHCl_3}$ cm$^{-1}$: 3330

EXAMPLE 15

(1) Synthesis of 1-(2,2,5-Trimethylcyclopent-5-enyl)Oct-1-en-3-one

The entitled compound was obtained from 4-(2,2,5-trimethylcyclopent-5-enyl)but-3-en-2-one and n-butyl iodide in the same manner as in Example 2-(1).

IR $\nu_{max}^{CHCl_3}$ cm$^{-1}$: 1680

(2) Synthesis of 1-(2-Hydroxy-2,2,5-Trimethylcyclopentyl)Oct-1-en-3-ol

The entitled compound was obtained from 1-(2,5,5-trimethylcyclopent-5-enyl)oct-1-en-3-one in the same manner as in Example 1-(4), (5), and (6).

IR $\nu_{max}^{CHCl_3}$ cm$^{-1}$: 3600, 3330

EXAMPLE 16

Synthesis of 1-(2,4-Dihydroxy-2,6,6-Trimethylcyclohexl)Hex-1-yn-3-ol

To a solution of 1.28 g of 1-(2,4-dihydroxy-2,6,6-trimethylcyclohexyl)hex-1-en-3-ol in 50 ml of triethylamine was slowly added 1.2 ml of acetic anhydride under ice-cooling. To the mixture was further added 120 mg of p-dimethylaminopyridine. The mixture was allowed to stand at room temperature overnight. The reaction mixture was poured onto ice and extracted with diethyl ether. The extract was washed successively with a 0.5N hydrochloric acid aqueous solution and a saturated sodium chloride aqueous solution and dried over anhydrous magnesium sulfate, followed by filtration. The filtrate was concentrated under reduced pressure to obtain 1.25 g of a triacetate compound as an oily product. The resulting triacetate compound (1.21 g) was dissolved in 130 ml of carbon tetrachloride, followd by cooling to −5° C. to 0° C. with ice-cold sodium chloride. To the solution was slowly added dropwise 8.3 ml of bromine. After completion of the addition, the mixture was allowed to stand at 0° C. for 1 hour, washed successively with a 10% aqueous solution of sodium hydrogen carbonate and a saturated sodium chloride aqueous solution, and dried over ahhydrous magnesium sulfate. After filtration, the filtrate was concetrated under reduced pressure to obtain 1.95 g of an oily product.

Separetely, 16 g of potassium t-butoxide was dissolved in 21 ml of dry dimethyl sulfoxide (hereinafter "DMSO"), and a solution of 1.9 g of the above prepared dibromide in 5 ml of DMSO was added thereto over 10 minutes, followed by heating at 50° C. for 1 hour. The reaction mixture was poured into 100 ml of water and extracted with diethyl ether. The extract was washed successively with water and a saturated sodium chloride aqueous solution, and dried. After filtration, the filtrate was concentrated under reduced pressure to obtain 1.5 g of an acetylene triacetate compound.

The resulting acetate compound was dissolved in 80 ml of dry methanol, and 15 g of potassium carbonate was added to the solution under ice-cooling, followed by stirring for 2 hours. The reaction mixture was poured into 50 ml of water and extracted with diethyl ether. The extract was worked-up in a usual manner to obtain 0.9 g of a crude triol compound. Purification by silica gel column chromatography gave 0.73 g (yield: 57%) of the entitled compound.

IR $\nu_{max}^{CHCl3}$ cm$^{-1}$: 3300, 1150, 1100

EXAMPLE 17

(1) Synthesis of 1-(1,2-Dihydroxy-2,6,6-Trimethylcyclohexyl)Oct-1-yn-3-ol

To 6.5 ml of a 1.6M n-hexane solution of n-butyl lithium was added 20 ml of anhydrous THF at −78° C. (bath temperature) in a nitrogen atmosphere, and 2.2 g of a tetrahydropyranyl ether of 1-octyn-3-ol was added dropwise thereto under the same conditions over 10 minutes. After the addition, the mixture was stirred for 30 minutes. Then, 30 ml of an anhydrous THF solution containing 2.0 g of 2-trimethylsiloxy-2,6,6-trimethylcyclohexanone was added dropwise to the mixture under the same conditions over 35 minutes. After the dropwise addition, the mixture was stirred for 5 hours. A saturated ammonium chloride aqueous solution was added to the reaction mixture, and the mixture was extracted with diethyl ether. The diethyl ether was removed from the extract by distillation, a 1N hydrochloric acid aqueous solution and methanol were added to the residue, followed by stirring at room temperature for 5 hours. The methanol was removed by distillation under reduced pressure, and the residue was extracted with diethyl ether. The organic layer was dried over anhydrous magnesium sulfate, and the solvent, etc. were removed by distillation under reduced pressure. The residue was purified by silica gel column chromatography to obtain 1.8 g (yield: 70%) of 1-(1,2-dihydroxy-2,6,6-trimethylcyclohexyl)oct-1-yn-3-ol.

IR $\nu_{max}^{CHCl3}$ cm$^{-1}$: 3300

(2) Synthesis of 1-(2-Hydroxy-2,6,6-Trimethylcyclohexylidene)Oct-1-en-3-ol

To 5 ml of an anhydrous THF suspension containing 274 mg of lithium aluminum hydride was slowly added 10 ml of an anhydrous THF solution containing 1.0 g of 1-(1,2-dihydroxy-2,6,6-trimethylcyclohexyl)oct-1-yn-3-ol under ice-cooling in a nitrogen atmosphere. After the addition, the mixture was placed under refluxing conditions and stirred for 10 hours. After completion of the reaction, the reaction mixture was cooled, and 0.3 ml of water, 0.3 ml of a 15% sodium hydroxide aqueous solution, and 1.0 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 568 mg (yield: 60%) of 1-(2-hydroxy-2,6,6-trimethylcyclohexylidene)oct-1-en-3-ol.

IR $\nu_{max}^{CHCl3}$ cm$^{-1}$: 3350, 1955

EXAMPLE 18

Synthesis of 1-(2-Hydroxy-2,6,6-Trimethylcyclohexylidene)Pent-1-en-3-ol

The entitled compound was obtained by using a tetrahydropyranyl ether of 1-pentyn-3-ol in the same manner as in Example 17.

IR $\nu_{max}^{CHCl3}$ cm$^{-1}$: 3350, 1960

EXAMPLE 19

Synthesis of 1-(2-Hydroxy-2,6,6-Trimethylcyclohexylidene)Hex-1-en-3-ol

The entitled compound was obtained by using a tetrahydropyranyl ether of 1-hexyn-3-ol in the same manner as in Example 17.

IR $\nu_{max}^{CHCl3}$ cm$^{-1}$: 3350, 1960

EXAMPLE 20

(1) Synthesis of 1-(1,2,4-Trihydroxy-2,6,6-Trimethylcyclohexyl)Oct-1-yn-3-ol

To 2.8 ml of a 1.6M n-hexane solution of n-butyl lithium was added 10 ml of anhydrous THF at −78° C. (bath temperature) in a nitrogen atmosphere, and 1.1 g of a tetrahydropyranyl ether of 1-octyn-3-ol was added dropwise thereto under the same conditions. After the addition, the mixture was stirred for 30 minutes. Then, 15 ml of an anhydrous THF solution containing 1.4 g of 2,4-bis(trimethylsiloxy)-2,6,6-trimethylcyclohexanone was added dropwise to the mixture under the same conditions over 20 minutes. After the dropwise addition, the mixture was stirred for 5 hours. A saturated ammonium chloride aqueous solution was added to the reaction mixture, and the mixture was extracted with diethyl ether. The diethyl ether was removed from the extract by distillation, and a 1N hydrochloric acid aqueous solution and methanol were added to the residue, followed by stirring at room temperature for 6 hours. The methanol was removed by distillation under reduced pressure, and the residue was extracted with diethyl ether. The organic layer was dried over anhydrous magnesium sulfate, and the solvent, etc. were removed by distillation under reduced pressure. The residue was purified by silica gel column chromatography to obtain 1.1 g (yield: 85%) of 1-(1,2,4-trihydroxy-2,6,6-trimethylcyclohexyl)oct-1-yn-3-ol.

IR $\nu_{max}^{CHCl_3}$ cm$^{-1}$: 3300

(2) Synthesis of 1-(2,4-Dihydroxy-2,6,6-Trimethylcyclohexylidene)Oct-1-en-3-ol

To 10 ml of an anhydrous THF suspension containing 383 mg of lithium aluminum hydride was slowly added 10 ml of an anhydrous THF solution containing 1.0 g of 1-(1,2,4-trihydroxy-2,6,6-trimethylcyclohexyl)-oct-1-yn-3-ol over 10 minutes under ice-cooling in a nitrogen atmosphere. After the addition, the mixture was placed under refluxing conditions and stirred for 15 hours. After completion of the reaction, the reaction mixture was cooled, and 0.4 ml of water, 0.4 ml of a 15% sodium hydroxide aqueous solution, and 1.2 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 596 mg (yield: 63%) of 1-(2,4-dihydroxy-2,6,6-trimethylcyclohexylidene)oct-1-en-3-ol.

IR $\nu_{max}^{CHCl_3}$ cm$^{-1}$: 3350, 1955

EXAMPLE 21

Synthesis of 1-(2,4-Dihydroxy-2,6,6-Trimethylcyclohexylidene)-Pent-1-en-3-ol

The entitled compound was obtained by using a tetrahydropyranyl ether of 1-pentyn-3-ol in the same manner as in Example 20.

IR $\nu_{max}^{CHCl_3}$ cm$^{-1}$: 3330, 1955

EXAMPLE 22

Synthesis of 1-(2,4-Dihydroxy-2,6,6-Trimethycyclohexylidene)Hex-1-en-3-ol

The entitled compound was obtained by using a tetrahydropyranyl ether of 1-hexyn-3-ol in the same manner as in Example 20.

IR $\nu_{max}^{CHCl_3}$ cm$^{-1}$: 3330, 1955

EXAMPLE 23

(1) Synthesis of 4-(1,2-Dihydroxy-2,5,5-Trimethylcyclopentyl)But-3-yn-2-ol

To 7.3 ml of a 1.6M n-hexane solution of n-butyl lithium was added 20 ml of anhydrous THF at $-78°$ C. (bath temperature) in a nitrogen atmosphere, and 1.8 g of a tetrahydropyranyl ether of 3-butyn-2-ol was added dropwise thereto under the same conditions over 10 minutes. After the addition, the mixture was stirred for 30 minutes. Then, 30 ml of an anhydrous THF solution containing 2.1 g of 2-trimethylsiloxy-2,5,5-trimethylcyclopentanone was added dropwise to the mixture under the same conditions over 30 minutes. After the dropwise addition, the mixture was stirred for 5 hours. A saturated ammonium chloride aqueous solution was added to the reaction mixture, and the mixture was extracted with diethyl ether. After the diethyl ether was removed from the extract by distillation, a 1N hydrochloric acid aqueous solution and methanol were added to the residue, followed by stirring at room temperature for 5 hours. The methanol was removed by distillation under reduced pressure, and the residue was extracted with diethyl ether. The organic layer was dried over anhydrous magnesium sulfate, and the solvent, etc. were removed by distillation under reduced pressure. The residue was purified by silica gel column chromatography to obtain 2.1 g (yield: 75%) of 4-(1,2-dihydroxy-2,5,5-trimethylcyclopentyl)but-3-yn-2-ol.

IR $\nu_{max}^{CHCl_3}$ cm$^{-1}$: 3300

(2) Synthesis of 4-(2-Hydroxy-2,5,5-Trimethylcyclopentylidene)But-3-en-ol

To 15 ml of an anhydrous THF suspension containing 717 mg of lithium aluminum hydride was slowly added 20 ml of an anhydrous THF solution containing 2.0 g of 4-(1,2-dihydroxy-2,5,5-trimethylcyclopentyl)but-3-yn-2-ol under ice-cooling in a nitrogen atmosphere over 10 minutes. After the addition, the mixture was placed under refluxing conditions and stirred for 15 hours. After completion of the reaction, the reaction mixture was cooled, and 0.7 ml of water, 0.7 ml of a 15% sodium hydroxide aqueous solution, and 2.1 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 1.2 g (yield: 63%) of 4-(2-hydroxy-2,5,5-trimethylcyclopentylidene)but-3-en-2-ol.

IR $\nu_{max}^{CHCl_3}$ cm$^{-1}$: 3600, 3350, 1960

EXAMPLE 24

Synthesis of 1-(2-Hydroxy-2,5,5-Trimethylcyclopentylidene)Pent-1-en-3-ol

The entitled compound was obtained by using a tetrahydropyranyl ether of 1-pentyn-3-ol in the same manner as in Example 23.

IR $\nu_{max}^{CHCl_3}$ cm$^{-1}$: 3600, 3350, 1960

EXAMPLE 25

Synthesis of 1-(2-Hydroxy-2,5,5-Trimethylcyclopentylidene)Hex-1-en-3-ol

The entitled compound was obtained by using a tetrahydropyranyl ether of 1-hexyn-3-ol in the same manner as in Example 23.

IR $\nu_{max}^{CHCl_3}$ cm$^{-1}$: 3600, 3350, 1960.

EXAMPLE 26

Synthesis of 1-(2,4-Dihydroxy-2,5,5-Trimethylcyclopentylidene)Oct-1-en-3-ol

The entitled compound was obtained by using a tetrahydropyranyl ether of 1-octyn-3-ol in the same manner as in Example 23.

IR $\nu_{max}^{CHCl_3}$ cm$^{-1}$: 3600, 3350, 1960

EXAMPLE 27

(1) Synthesis of 4-(1,2,4-Trihydroxy-2,5,5-Trimethylcyclopentyl)But-3-en-2-ol

To 5.2 ml of a 1.6M n-hexane solution of n-butyl lithium was added 15 ml of anhydrous THF at $-78°$ C. (bath temperature) in a nitrogen atmosphere, and 1.3 g of a tetrahydropyranyl ether of 3-butyn-3-ol was added dropwise thereto under the same conditions over 10 minutes. After the addition, the mixture was stirred for 30 minutes. Then, 20 ml of an anhydrous THF solution containing 2.1 g of 2,4-bis(trimethylsiloxy)-2,5,5-trimethylcyclohexanone was added dropwise to the mixture under the same conditions over 20 minutes. After the dropwise addition, the mixture was stirred for 5 hours. A saturated ammonium chloride aqueous solution was added to the reaction mixture, and the mixture was extracted with diethyl ether. After the diethyl ether was removed from the extract by distillation, a 1N hydrochloric acid aqueous solution and methanol were added to the residue, followed by stirring at room temperature for 5 hours. The methanol was removed by distillation under reduced pressure, and the residue was extracted with diethyl ether. The organic layer was dried over anhydrous magnesium sulfate, and the solvent, etc. were removed by distillation under reduced pressure. The residue was purified by silica gel column chromatography to obtain 1.1 g (yield: 70%) of 4-(1,2,4-trihydroxy-2,5,5-trimethylcyclopentyl)but-3-en-2-ol.

IR $\nu_{max}^{CHCl_3}$ cm$^{-1}$: 3300

(2) Synthesis of 4-(2,4-Dihydroxy-2,5,5-Trimethylcyclopentylidene)-But-3-en-2-ol To 25 ml of an anhydrous THF suspension containing 583 mg of lithium aluminum hydride was slowly added 20 ml of an anhydrous THF solution containing 1.0 g of 4-(1,2,4-trihydroxy-2,5,5-trimethylcyclopentyl)but-3-en-2-ol under ice-cooling in a nitrogen atmosphere over 10 minutes. After the addition, the mixture was placed under refluxing conditions and stirred for 10 hours. After completion of the reaction, the reaction mixture was cooled, and 0.6 ml of water, 0.6 ml of a 15% sodium hydroxide aqueous solution, and 1.8 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 509 mg (yield: 55%) of 4-(2,4-dihydroxy-2,5,5-trimethylcyclopentylidene)but-3-en-2-ol.

IR $\nu_{max}^{CHCl_3}$ cm$^{-1}$: 3600, 3350, 1960

EXAMPLE 28

Synthesis of 1-(2,4-Dihydroxy-2,5,5-Trimethylcyclopentylidene)-Pent-1-en-3-ol

The entitled compound was obtained by using a tetrahydropyranyl ether of 1-pentyn-3-ol in the same manner as in Example 27.

IR $\nu_{max}^{CHCl_3}$ cm$^{-1}$: 3330, 1960

EXAMPLE 29

Synthesis of 1-(2,4-Dihydroxy-2,5,5-Trimethylcyclopentylidene)-Hex-1-en-3-ol

The entitled compound was obtained by using a tetrahydropyranyl ether of 1-hexyn-3-ol in the same manner as in Example 27.

IR $\nu_{max}^{CHCl_3}$ cm$^{-1}$: 3300, 1960

EXAMPLE 30

Synthesis of 1-(2,4-Dihyroxy-2,5,5-Trimethylcyclopentylidene)Oct-1-en3-ol

The entitled compound was obtained by using a tetrahydropyranyl ether of 1-octyn-3-ol in the same manner as in Example 27.

IR $\nu_{max}^{CHCl_3}$ cm$^{-1}$: 3300, 1960

EXAMPLE 31

(1) Synthesis of 2-Acetoxy-4-(1,2-Epoxy-2,5,5-Trimethylcyclopentyl)-But-3-yn

To 70 ml of an anhydrous chloroform solution containing 2.4 g of 2-acetoxy-4-(2,5,5-trimethylcyclopent-5-enyl)but-3-yn was slowly added 2.3 g of m-chloroperbenzoic acid under ice-cooling. After the addition, the mixture was stirred under the same conditions for 5 hours. After completion of the reaction, the reaction mixture was washed several times with a saturated aqueous solution of sodium hydrogen carbonate. The organic layer was further washed successively with a saturated sodium chloride aqueous solution and water, and dried over anhydrous magnesium sulfate. The solvent, etc. were removed by distillation under reduced pressure, and the residue was purified by silica gel column chromatography to obtain 2.3 g (yield: 87%) of 2-acetoxy-4-(1,2-epoxy-2,5,5-trimethylcyclopentyl)-but-3-yn.

IR $\nu_{max}^{CHCl_3}$ cm$^{-1}$: 1730

(2) Synthesis of 4-(2-Hydroxy-2,5,5-Trimethylcyclopentylidene)But-3-en-2-ol

To 20 ml of an anhydrous THF suspension containing 644 mg of lithium aluminum hydride was slowly added 20 ml of an anhydrous THF solution containing 2.0 g of 2-acetoxy-4-(1,2-epoxy-2,5,5-trimethylcyclopentyl)but-3-yn under ice-cooling in a nitrogen atmosphere over 10 minutes. After the addition, the mixture was placed under refluxing conditions and stirred for 10 hours. After completion of the reaction, the reaction mixture was cooled, and 0.6 ml of water, 0.6 ml of a 15% sodium hydroxide aqueous solution, and 1.8 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 1.2 g (yield: 70%) of 4-(2-hydroxy-2,5,5-trimethylcyclopentylidene)but-3-en-2-ol.

IR $\nu_{max}^{CHCl_3}$ cm$^{-1}$: 3600, 3350, 1960

EXAMPLE 32

Synthesis of 2-Acetoxy-4-(4-Acetoxy-1,2-Epoxy-2,5,5-Trimethylcyclopentyl)But-3-yn To 100 ml of an anhydrous chloroform solution containing 3.4 g of 2-acetoxy-4-(3-acetoxy-2,5,5-trimethylcyclopent-5-enyl)but-3-yn was slowly added 2.7 g of m-chloroperbenzoic acid under ice-cooling. After the addition, the mixture was stirred under the same conditions for 8 hours. After completion of the reaction, the reaction mixture was washed several times with a saturated aqueous solution of sodium hydrogen carbonate.

The organic layer was further washed successively with a saturated sodium chloride aqueous solution and water, and dried over anhydrous magnesium sulfate. The solvent, etc. were removed by distillation under reduced pressure, and the residue was purified by silica gel column chromatography to obtain 2.6 g (yield: 72%) of 2-acetoxy-4-(4-acetoxy-1,2-epoxy-2,5,5-trimethylcyclopentyl)but-3-yn.

IR $\nu_{max}^{CHCl_3}$ cm$^{-1}$: 1730

(2) Synthesis of 4-(2,4-Dihydroxy-2,5,5-Trimethylcyclopentylidene)-But-3-en-2-ol To 30 ml of an anhydrous THF suspension containing 808 mg of lithium aluminum hydride was slowly added 35 ml of an anhydrous THF solution containing 2.0 g of 2-acetoxy-4-(4-acetoxy-1,2-epoxy-2,5,5-trimethylcyclopentyl)but-3-yn under ice-cooling in a nitrogen atmosphere over 10 minutes. After the addition, the mixture was placed under refluxing conditions and stirred for 8 hours. After completion of the reaction, the reaction mixture was cooled, and 0.8 ml of water, 0.8 ml of a 15% sodium hydroxide aqueous solution, and 2.4 ml of water were carefully added thereto in this order, followed by vigorously stirring for 20 minutes. Any insoluble matter was removed by filtration with suction, and the filtrate was concentrated under reduced pressure. The resulting solid was purified by silica gel column chromatography to obtain 902 mg (yield: 60%) of 4-(2,4-dihydroxy-2,5,5-trimethylcyclopentylidene)but-3-en-2-ol.

IR $\nu_{max}^{CHCl_3}$ cm$^{-1}$: 3600, 3350, 1960

While the invention has been described in detail and with reference to specific embodiments thereof, it will be apparent to one skilled in the art that various changes and modifications can be made therein without departing from the spirit and scope thereof.

What is claimed is:

1. A cycloalkane derivative represented by formula (I):

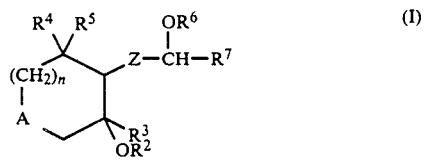

wherein A represents a methylene group, >CH—O—R$^8$, or a carbonyl group; R$^2$, R$^6$, and R$^8$ each represents a hydrogen atom or an organic residual group; R$^3$, R$^4$, and R$^5$ each represents a hydrogen atom or a substituted or unsubstituted alkyl group; R$^7$ represents a substituted or unsubstituted alkyl group; Z represents an ethynylene group (—C≡C—), a vinylene group, an ethylene group, or =C=CH—; and n=0 or 1, except that the cycloalkane is not represented by the case where R$^2$ and R$^6$ each represents a hydrogen atom, R$^3$, R$^4$, R$^5$, and R$^7$ each represents a methyl group, Z represents =C=CH— and n represents 1.

2. The cycloalkane derivative as claimed in claim 1, wherein the alkyl group represented by Group R$^3$, R$^4$, R$^5$ and R$^7$ contains from 1 to 7 carbon atoms.

3. The cycloalkane derivative as claimed in claim 2, wherein the alkyl group represented by Group R$^3$, R$^4$, R$^5$ and R$^7$ contains from 1 to 4 carbon atoms.

4. The cycloalkane derivative as claimed in claim 1, wherein said organic residual group for R$^2$, R$^6$ R$^8$ is selected from the group consisting of an alkyl group, an acyl group, an alkoxycarbonyl group, an alkoxycarboxylalkyl group, a carbonylalkyl group, a carboxyalkylcarbonyl group, a cyclic acetal group and an oligosaccharide residue having 1 to 3 sugar units.

5. An anti-peptic ulcer composition comprising an anti-peptic ulcer effective amount of the cycloalkane derivative of claim 1 and a pharmaceutically acceptable carrier or diluent.

6. The anti-peptic ulcer composition as claimed in claim 5, wherein said anti-peptic ulcer effective amount is from 0.001 to 0.1 mg/kg of body weight.

* * * * *